United States Patent [19]

Graham

[11] Patent Number: 4,484,583

[45] Date of Patent: Nov. 27, 1984

[54] ESOPHAGEAL STETHOSCOPE

[76] Inventor: John R. Graham, 14 Lee Ave., White Plains, N.Y. 10606

[21] Appl. No.: 267,046

[22] Filed: May 26, 1981

[51] Int. Cl.³ .............................................. A61B 5/02
[52] U.S. Cl. .................................. 128/671; 128/715; 128/773
[58] Field of Search ............... 128/642, 673, 725, 736, 128/773, 303.15, 348, 349 R, 4, 670–671, 715, 665–666

[56] References Cited

U.S. PATENT DOCUMENTS

| | | | |
|---|---|---|---|
| 3,357,433 | 12/1967 | Fourestier et al. | 128/4 X |
| 3,499,434 | 3/1970 | Ullrich et al. | 128/670 |
| 3,499,435 | 3/1970 | Rockwell et al. | 128/671 |
| 3,633,585 | 1/1972 | McDonald, Jr. | 128/348 |
| 3,884,219 | 5/1975 | Richardson et al. | 128/736 X |
| 3,951,136 | 4/1976 | Wall | 128/642 |
| 4,036,211 | 7/1977 | Veth et al. | 128/671 X |
| 4,091,803 | 5/1978 | Pinder | 128/666 |
| 4,176,660 | 12/1979 | Mylrea et al. | 128/671 |
| 4,301,809 | 11/1981 | Pinchak | 128/715 X |
| 4,304,240 | 12/1981 | Perlin | 128/671 |
| 4,331,156 | 5/1982 | Apple et al. | 128/715 X |

OTHER PUBLICATIONS

Yeung et al., "Electrooptical Sensor for Cardiac Sound and Vibrations," IEEE Trans. on Biomed. Engr.; vol. BME-24, No. 1, pp. 73–75, Jan. 1977.

Primary Examiner—Lee S. Cohen
Assistant Examiner—Angela D. Sykes
Attorney, Agent, or Firm—Toren, McGeady and Stanger

[57] ABSTRACT

An esophageal stethoscope includes a plastic tube having at least one bore extending over the length of the tube. The tube has a distal end which is insertable into the esophagus of the patient, and a proximal end for providing respiratory and heart sounds produced at the distal end and transmitted through the tube for monitoring. A microphone element is mounted in the bore of the tube at the distal end for detecting the respiratory and heart sounds, and providing corresponding electrical signals. The signals are conducted through wires arranged in the tube bore to the proximal end of the tube where the wires are connected to a terminal member. Accordingly, the heart and respiratory sounds can be reproduced with maximal signal to noise ratio when the terminal member is connected to a suitable amplifier and speaker arrangement, or other signal processing equipment.

7 Claims, 3 Drawing Figures

ESOPHAGEAL STETHOSCOPE

BACKGROUND OF THE INVENTION

1. Field of the Invention

The present invention is directed to esophageal stethoscopes, and specifically to an esophageal stethoscope including a microphone element at its distal end for detecting heart and respiratory sounds produced by a patient when the stethoscope is inserted into the patient's esophagus.

2. Description of the Prior Art

Conventional esophageal stethoscopes include a length of plastic tubing one end of which, the distal end, may have a number of openings formed through the tube wall and a relatively thin protective covering sealed over the openings to prevent body fluids from entering the tube when the distal end is inserted into a patient's esophagus. The other end of the tube, i.e., the proximal end, may be connected to a fitting such as a "Luer" type of fitting for connecting with a set of stethoscope earpieces.

Esophageal stethoscopes are often used by anesthesiologists who listen to the heart and respiratory sounds of a patient during the course of a surgical procedure. The anesthesiologist listens for changes in the heart or respiratory sounds which serve to indicate the existence of a problem requiring the immediate attention of the anesthesiologist. In the event the anesthesiologist must be located a considerable distance from the patient during a surgical or other operating procedure, it will be understood that the length of the stethoscope tubing must be correspondingly increased in order that it remain connected with the stethoscope earpieces which must always be worn by the anesthesiologist. However, as the length of the tubing is increased, the intensity of the sounds reaching the proximal end of the tubing diminishes accordingly. Further, there are instances when the anesthesiologist must move about the operating room to attend to required tasks. This requires that the tubing be temporarily disconnected from the stethoscope earpieces, so that the patient's heart and respiratory sounds are not monitored during such times. This presents a potential hazard for the patient.

It is also known to provide a microphone at one end of a length of flexible tubing so as to convert heart sounds picked up by a chest piece at the other end of the tubing into electrical impulses. For example, U.S. Pat. No. 2,699,465 issued Jan. 11, 1955, to S. Hamilton shows such an arrangement which is used in a warning system for indicating the cessation of cardiac funtions. Another device is also known in which the proximal end of an esophageal stethoscope is provided with a Luer fitting for coupling with a microphone of an FM transmitter, thereby allowing sounds conveyed to the proximal end of the tubing to be monitored by a receiver at a location remote from the operating table.

It will be appreciated, however, that the placement of a microphone at the proximal end of a stethoscope tube will result in the detection and reproduction of sounds developed over the entire length of the tube which sounds may not be among those desired to be heard. For example, bending movement of the stethoscope tube will produce noises at the proximal end of the tube and, since the microphone is unable to discriminate between these noises and the respiratory and heart sounds originating from the distal end of the tube, these noises will be converted into electrical signals thus making the monitoring of the heart and breathing sounds more difficult.

SUMMARY OF THE INVENTION

An object of the present invention is to overcome the above and other shortcomings in the known esophageal stethoscopes.

Another object of the invention is to provide an esophageal stethoscope which provides a relatively high signal to noise ratio where the desired signal corresponds to a patient's heart and breathing sounds against the background of all other physiologically and environmentally produced noise.

Another object of the invention is to provide a stethoscope in which distortion of the heart and breathing sounds resulting from tubing length, diameter or flexure is virtually non-existent.

Another object of the invention is to provide an esophageal stethoscope having high sensitivity such as to allow monitoring of heart and breathing sounds produced at its distal end, which sounds have not heretofore been made audible, at the proximal end of the stethoscope.

Another object of the invention is to provide an esophageal stethoscope having high noise immunity, thereby being much less susceptible to audio interference normally encountered with the conventional stethoscopes when the tubing is physically disturbed or contacted.

In accordance with the present invention, an esophageal stethoscope includes a plastic tube having at least one bore extending over its length, a distal end for insertion in the esophagus of a patient and a proximal end for providing breath and heart sounds produced in the vicinity of the distal end for monitoring. An audio transducer element is mounted in the bore of the tube at the distal end for detecting the breath and heart sounds and providing corresponding electrical signals. Means arranged in the bore and coupled to the microphone element operate to conduct the microphone signals to the proximal end of the tube, and terminal means coupled to the conducting means at the proximal end of the tube provides the microphone signals for further processing.

The esophageal stethoscope of the present invention is particularly advantageous because it not only provides high quality reproduction of the actual heart and breath sounds, but also, the sounds are reproduced free from interference by extraneous noise caused by the physical make up of the stethoscope. Additionally, one can obtain equally excellent results regardless of whether 12, 18 or 24 FR. diameter tubing is used.

The various features of novelty which characterize the invention are pointed out with particularity in the claims annexed to and forming a part of this disclosure. For a better understanding of the invention, its operating advantages and specific objects attained by its use, reference should be had to the drawings and descriptive matter in which there are illustrated and described preferred embodiments of the invention.

DETAILED DESCRIPTION OF THE INVENTION

Figure 1:
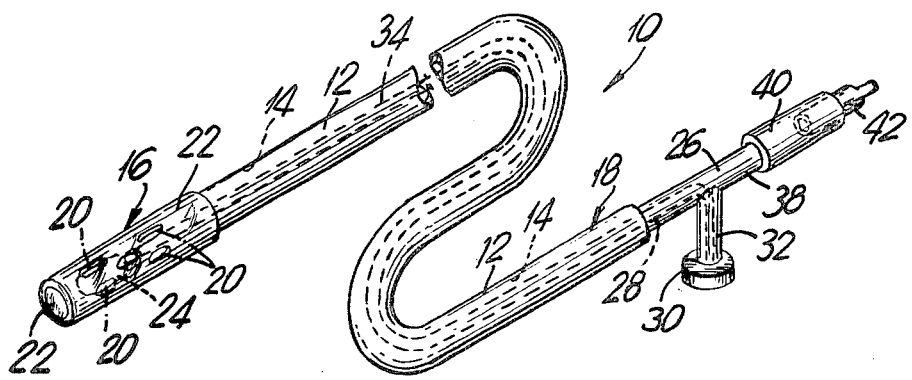
FIG. 1 is a perspective, fragmented view of an esophageal stethoscope according to the invention.

FIG. 1 is a perspective view of an esophageal stethoscope according to the invention. Basically, the stethoscope 10 includes a length of plastic tubing 12 which can be of any of the conventional types of tubing used for esophageal stethoscopes such as, for example, tubing sold under the trade name "Silastic" by Dow Corning Corporation. Tubing 12 has an axial bore 14 extending over its length between a distal end 16 which is insertable into a patient's esophagus, and a proximal end 18 opposite the distal end 16 whereat breath and heart sounds produced in the vicinity of the distal end can be monitored, as explained below.

The distal end 16 of the tubing 12 has a number of acoustic openings 20 through the wall of the tubing 12 to enable sounds to enter within the bore 14 of the tube 12 at the distal end 16. A relatively thin wall protective cap 22 is provided over the distal end of the tube 12 to cover the acoustic openings 20 and thus prevent body fluids from entering within the tube bore 14. Cap 22 may be the same type of cap provided at the distal end of a conventional esophageal stethoscope, and can be sealed at the distal end 16 of the tube 12 with conventional bonding techniques, e.g., heat bonding, high frequency treatment, or PVC glue or similar adhesive.

An audio transducer element 24 is mounted at the distal end 16 of the tube bore 14 and can be fixed in position by way of a force fit within the tube wall. This audio transducer element can be any type of device which can sense the audio input from the heart and breath sounds and convert them to corresponding electrical signals, e.g., a microphone, pressure transducer or the fiber optic embodiment described hereinafter. For purposes of simplification, element 24 will hereinafter be discussed in terms of a microphone element. If necessary, microphone element 24 can be further supported with silicone adhesive deposited only along the edges of the element 24 in an amount just sufficient to prevent movement. One type of microphone element 24 which has been used is Model No. EA 1934, manufactured by Knowles Electronics Inc. of Franklin Park, Ill. This element is an electret type, but a ceramic type such as Model No. BL 1785 of the same manufacturer can also be used. The latter model has a frequency range of from 20 to 10,000 Hertz with a nominal sensitivity at 1000 Hertz of −69 dB relative to one volt per microbar.

At the proximal end 18 of tube 12 there is provided a T connector 26 having a branch 28 fitted at the proximal end of tube 12 to communicate with the bore 14. A conventional electrical connector 30 is fitted on a second branch 32 of the T connector 26. A pair of wire leads 34 is routed through the tube bore 14, the leads 34 being connected at the distal end 16 to the microphone element 24. The leads 34 are connected at the proximal end 18 to the electrical connector 30 so that signals provided by the microphone element 24 and conducted by the leads 34 through the tube 10 are made available for further processing at the connector 30.

A third branch 38 of the T connector 26 is coupled through a short length of tubing 40 to a conventional Luer connector 42. This arrangement allows audible sounds conducted through the tube bore 14 from the distal end 16 of the tube to be monitored with a set of conventional stethoscope earpieces when the earpieces are connected to the Luer connector 42. Accordingly, the present stethoscope 10 allows for monitoring of a patient's heart and breath sounds either by way of equipment which audibly reproduces the sounds in response to the electrical signals provided by the microphone element 24 at the connector 30, or with the aid of a conventional set of stethoscope earpieces when coupled to the Luer connector 42. This feature is important in that should the microphone element 24 or other audio components fail during the course of an operating procedure on a patient, the patient's heart and breath sounds can still be monitored by coupling stethoscope earpieces to the Luer connector 42.

Figure 3:
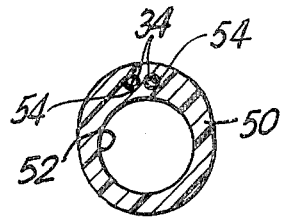
FIG. 3 is a sectional view of one form of plastic tubing which can be used for the stethoscope of FIG. 1.

FIG. 3 shows a modification of tube 12 in FIG. 1 wherein a tube 50 of "Silastic" silicone material is provided, the tube 50 having a first bore 52 for audibly conducting the heart and breath sounds produced at the distal end 16 to the proximal end 18 of the tube 50, and second bores 54 for containing the wire leads 34 and routing the leads 34 between the microphone element 24 (not shown) and the electrical connector 30 (not shown), similar to the arrangement of FIG. 1. Preferably, the cross-section of the second bores 54 should be just sufficient to prevent the wire leads 34 from moving relative to the tube 50, so that audible noise originating from the wire leads themselves will be suppressed when the tube 50 is flexed as often occurs during use. It is also possible in this case for leads 34 to be molded separately into the wall of tube 50. Such noise originating from movement of the leads 34 relative to the interior of the tube 50 would otherwise be heard when a set of stethoscope earpieces is coupled onto the Luer connector 42. Tubing having a cross-section similar to that of tube 50 is also known and may be obtained from Dow Corning Corporation under the "SILASTIC" name.

Figure 2:
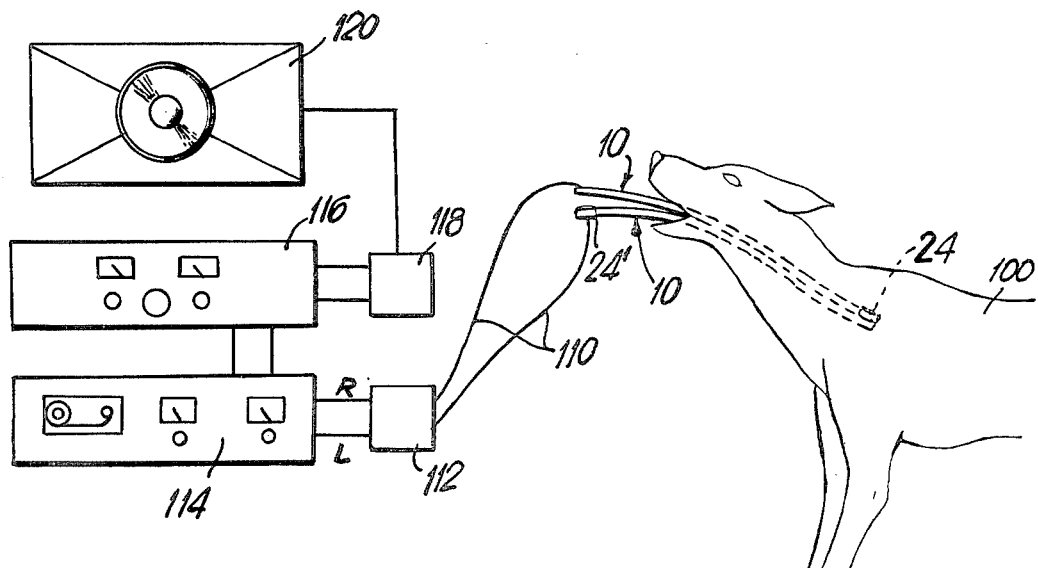
FIG. 2 is a schematic diagram showing a test measurement system for evaluating the performance of the esophageal stethoscope of FIG. 1.

FIG. 2 shows an arrangement for measuring the performance of the present stethoscope 10 relative to the conventional esophageal stethoscope in which a microphone element is placed at the proximal, rather than the distal end of the stethoscope 10. The present stethoscope 10 and a comparison stethoscope 10' having a microphone element 24' at its proximal end were inserted together in the esophagus of a dog 100. The outputs of both microphones 24,24' were connected through identical cables 110 to a coupler device 112 which provided a 9-volt DC supply to both microphone elements 24,24' while simultaneously AC coupling the microphone elements 24,24' to a two-channel tape recorder 114. Accordingly, the signals provided by both microphone elements 24,24' were simultaneously recorded on tape. The outputs from the tape recorder were coupled to a conventional high-fidelity stereo amplifier 116, and the speaker outputs of the amplifier 116 were connected to a channel switch 118. Switch 118 was arranged to allow switching of either speaker output of the amplifier 116 to a single speaker 120 for instantaneous comparison.

As measured on the tape recorder level meters, the signals from the microphone element 24 of the present stethoscope 10 were 34 db higher than the signals provided simultaneously by the microphone element 24' of the comparison stethoscope 10'.

The present stethoscope 10 provides an extended frequency response which, if a microphone element such as type 1785, mentioned above, is used, can be as wide as from 20 Hz to over 10 kHz. The heart and breath sounds are transduced at the location of the heart and electrically transmitted through wires to an amplifier or other electrical signal processing equipment. Therefore, these sounds are not subject to the inherent attenuation due to the length, diameter or flexibility of the stethoscope tube.

With the recent trend toward the use of disposable medical devices, the present stethoscope 10 may be constructed in a disposable form which is economically feasible. Microphone element 24 may, for example, be plated or otherwise deposited at the distal end of the tube 12 (or 50) during the manufacturing process of forming the stethoscope tube. It is also possible to use an optic fiber in place of the wire leads 34 and allow the sound pressures developed at the distal end of the stethoscope to cause a thin diaphragm membrane to vibrate, and thereby modulate a beam of light directed toward the distal end of the optic fiber from a light-emitting diode mounted in the tube or a conventional fiber optic light source external to the stethoscope.

While specific embodiments of the invention have been shown and described in detail to illustrate the application of the inventive principles, it will be understood that the invention may be embodied otherwise without departing from such principles.

What is claimed is:

1. An esophageal stethoscope comprising a flexible plastic tube of a particular length and having a first bore extending over said length, said tube having a distal end for insertion in the esophagus of a patient and a proximal end opposite said distal end wherein said first bore audibly conducts breath and heart sounds produced in the vicinity of said distal end through said tube for monitoring at said proximal end, an audio transducer element mounted at said distal end of said tube for detecting the breath and heart sounds and providing output signals representative of the breath and heart sounds as produced only in the vicinity of said distal end, said audio transducer element being arranged in said tube so that said output signals are substantially unaffected by vibrations produced over the length of said tube outside the vicinity of said distal end, terminal means at the proximal end of said tube for providing said output signals for further processing, connecting means arranged in said tube and coupled to said audio transducer element for connecting said audio transducer element to said terminal means, and fitting means communicating with said first bore of said tube at said proximal end for enabling the heart and breath sounds audibly conducted by said first bore to be monitored by a stethoscope earpiece.

2. An esophageal stethoscope according to claim 1, including means coupled to said terminal means for audibly reproducing the heart and breath sounds in response to said signals.

3. An esophageal stethoscope according to claim 1, wherein said connecting means comprises a wire lead.

4. An esophageal stethoscope according to claim 1, wherein said tube has a second bore for containing said connecting means and preventing said connecting means from producing sounds which would otherwise be audibly conducted by said first bore.

5. An esophageal stethoscope according to claim 4, wherein said connecting means comprises wire leads and said second bore has a cross-section sufficient to prevent said wire leads from moving relative to said tube so that audible noise originating from said wire leads is suppressed when said tube is flexed.

6. An esophageal stethoscope according to claim 1, wherein said audio transducer element is at least partly plated on said distal end of said tube for insertion in the patient's esophagus.

7. An esophageal stethoscope according to claim 1, 2, 3, 4, 5 or 6 wherein said audio transducer element is a microphone.

* * * * *